United States Patent
Drahm et al.

(10) Patent No.: US 6,647,807 B2
(45) Date of Patent: *Nov. 18, 2003

(54) CORIOLIS MASS FLOW/DENSITY SENSOR WITH SINGLE STRAIGHT MEASURING TUBE

(75) Inventors: Wolfgang Drahm, Erding (DE); Georg Szaloky, Basel (CH); Alfred Wenger, Neftenbach (CH); Ennio Bitto, Asch (CH); Ole Koudal, Reinach (CH); Christian Matt, Lörrach (DE); Christian Schütze, Basel (CH)

(73) Assignee: Endress+Hauser Flowtec AG, Reinach (CH)

( * ) Notice: Subject to any disclaimer, the term of this patent is extended or adjusted under 35 U.S.C. 154(b) by 0 days.

This patent is subject to a terminal disclaimer.

(21) Appl. No.: 10/135,625

(22) Filed: Apr. 30, 2002

(65) Prior Publication Data

US 2002/0117010 A1 Aug. 29, 2002

Related U.S. Application Data

(62) Division of application No. 09/414,268, filed on Oct. 7, 1999, which is a continuation of application No. 08/940,644, filed on Sep. 30, 1997, now Pat. No. 6,006,609.
(60) Provisional application No. 60/032,906, filed on Dec. 16, 1996, and provisional application No. 60/036,192, filed on Jan. 21, 1997.

(30) Foreign Application Priority Data

Dec. 11, 1996 (EP) ............................................... 96119849
Jan. 16, 1997 (EP) ............................................... 97100582
Aug. 8, 1997 (EP) ............................................... 97810559

(51) Int. Cl.$^7$ ................................................. G01F 1/84
(52) U.S. Cl. ............................. 73/861.357; 73/861.355
(58) Field of Search ..................... 73/861.355, 861.356, 73/861.357

(56) References Cited

U.S. PATENT DOCUMENTS

| 4,187,721 A | 2/1980 | Smith |
| 4,524,610 A | 6/1985 | Fitzgerald et al. |
| 4,653,332 A | 3/1987 | Simonsen |
| 4,801,897 A | 1/1989 | Flecken |
| 4,872,351 A | 10/1989 | Ruesch |
| 4,876,879 A | 10/1989 | Ruesch |
| 4,938,075 A | 7/1990 | Lew |

(List continued on next page.)

FOREIGN PATENT DOCUMENTS

| EP | 0 469 448 A | 2/1992 |
| EP | 0 524 523 B1 | 1/1993 |
| EP | 0 547 455 A | 6/1993 |
| WO | WO 88 03642 | 5/1988 |
| WO | WO 95 03528 A | 2/1995 |

OTHER PUBLICATIONS

Wenger, Alfred P., *Vibrating Fluid Densimeters: A Solution to the Viscosity Problem*, Aug., 1980, IEEE Transactions on Industrial Electronics and Control Instrumentation, vol. IECI–27, No. 3, pp. 247–253.

Primary Examiner—Harshad Patel
(74) Attorney, Agent, or Firm—Bose McKinney & Evans LLP

(57) ABSTRACT

A Coriolis mass flow/density sensor is provided. The sensor includes a measuring tube for conducting a fluid. The measuring tube is fixed in a support and may be coupled to a pipe via an inlet tube and an outlet tube. The sensor further includes an excitation arrangement for vibrating the measuring tube in a predetermined vibration mode, a sensor arrangement for detecting vibrations of the measuring tube, and a brake assembly coupled to the measuring tube and the support. The brake assembly is operable to suppress at least one mode of vibrations other than the predetermined vibration mode.

40 Claims, 7 Drawing Sheets

U.S. PATENT DOCUMENTS

| | | |
|---|---|---|
| 5,027,662 A | 7/1991 | Titlow et al. |
| 5,253,533 A | 10/1993 | Lam et al. |
| 5,291,792 A | 3/1994 | Hussain et al. |
| 5,347,874 A | 9/1994 | Kalotay et al. |
| 5,351,561 A | 10/1994 | Wenger et al. |
| 5,365,794 A | 11/1994 | Hussain et al. |
| 5,476,013 A | 12/1995 | Hussain et al. |
| 5,531,126 A | 7/1996 | Drahm |
| 5,691,485 A | 11/1997 | Endo et al. |
| 5,796,010 A | 8/1998 | Kishio et al. |
| 5,796,012 A | 8/1998 | Gomi et al. |
| 6,006,609 A | 12/1999 | Drahm et al. |
| 6,401,548 B1 * | 6/2002 | Drahm et al. .......... 73/861.357 |

* cited by examiner

CORIOLIS MASS FLOW/DENSITY SENSOR WITH SINGLE STRAIGHT MEASURING TUBE

This application is a divisional of Ser. No. 09/414,268 filed Oct. 7, 1999 which is a continuation of Ser. No. 08/940,644 filed Sep. 30, 1997 U.S. Pat. No. 6,006,609 and claims benefit of Prov. No. 60/032,906 filed Dec. 16, 1996 and claims benefit of Prov. No. 60/036,192 filed Jan. 21, 1997.

FIELD OF THE INVENTION

This invention relates to a Coriolis mass flow/density sensor with a single straight measuring tube.

BACKGROUND OF THE INVENTION

U.S. Pat. No. 5,531,126 describes a Coriolis massflow/density sensor which can be installed in a pipe by means of a connecting element at the inlet end and a connecting element at the outlet end and through which a fluid to be measured flows during operation, comprising:

- a single straight measuring tube having a longitudinal axis and extending between and fixed to the connecting elements;
- a straight dummy tube extending parallel to the measuring tube and not traversed by the fluid;
- a nodal plate on an inlet side and a nodal plate on an outlet side,
  - one of which fixes the inlet-end portion of the measuring tube to the corresponding end portion of the dummy tube, and
  - the other of which fixes the outlet-end portion of the measuring tube to the corresponding end portion of the dummy tube, so that the measuring tube and the dummy tube are arranged side by side;
- a support tube having its ends fixed to the respective connecting elements and having a longitudinal axis of symmetry parallel to the longitudinal axis of the measuring tube; and
- means which act only on the dummy tube to excite the measuring tube into flexural vibrations whose frequency is not, however, identical with the resonance frequency of the measuring tube, with the measuring tube and the dummy tube vibrating in antiphase.

This prior-art Coriolis mass flow/density sensor is mechanically balanced only in a narrow range of density values—approximately± 5% of a rated density—for a given dimensional design, i.e., only at these density values will forces originating from the vibrations of the measuring tube be practically not transmitted via the connecting elements to the pipe. The above range is extended by the excitation "beside" the resonance frequency, but substantially more excitation energy is required than for excitation at the resonance frequency. The less balanced the mass flow/density sensor is, the more such forces and vibrational energy will be transmitted to the pipe; thus, however, vibrational energy is lost and measuring inaccuracy increases.

This unbalance has a disturbing effect not only in case of temperature-induced changes in the density of one and the same fluid but also particularly during the measurement of different fluids flowing in the pipe at different times, for example one after another.

SUMMARY OF THE INVENTION

Since Coriolis mass flow/density meters should be suitable for measuring as wide a range of very different fluids with different densities as possible, it is therefore important to provide Coriolis mass flow/density sensors which are balanced in the above sense over a wide density range and thus measure accurately.

To accomplish this, a first variant of the invention provides a Coriolis mass flow/density sensor which can be installed in a pipe and through which a fluid to be measured flows during operation, comprising:

- a single straight measuring tube having a longitudinal axis, an inlet end, and an outlet end;
- a support fixed to the inlet end and the outlet end,
  - a longitudinal centroidal line of which is parallel to, but does not coincide with, the longitudinal axis of the measuring tube;
- a cantilever
  - which is fixed to the measuring tube midway between the inlet end and the outlet end, and
  - which during operation causes the measuring tube to vibrate either in a first fundamental flexural mode or in a second fundamental flexural mode having a higher frequency than the first fundamental flexural mode;
- an excitation arrangement for constantly exciting the measuring tube in the second fundamental flexural mode
  - which is disposed approximately midway between the inlet end and the outlet end; and
- a sensor for the motions of the measuring tube on an inlet side and a sensor for the motions of the measuring tube on an outlet side which are located between the middle of the measuring tube and the inlet end and outlet end, respectively, at the same distance therefrom.

In a first preferred embodiment of the first variant of the invention, the support is a cylindrical tube having a wall of uniform thickness and a longitudinal axis which is parallel to, but does not coincide with, the longitudinal axis of the measuring tube.

In a second preferred embodiment of the first variant of the invention, the support is a cylindrical tube having a wall of only partially uniform thickness and a longitudinal axis which is parallel to, or coincides with, the longitudinal axis of the measuring tube, with the tube wall in the region of a first generating line diametrically opposite the cantilever being at least partially thicker than the uniform wall thickness and/or the tube wall in the region of a first generating line adjacent to the cantilever being at least partially thinner than the uniform wall thickness in order to form a counterbalance.

According to a development of the second embodiment of the first variant of the invention, a counterweight is attached, partially inserted in, or integrally formed on the tube wall diametrically opposite the cantilever.

In a third preferred embodiment of the first variant of the invention, which can be used in the above embodiments and the development of the second embodiment, the cantilever has the form of a plate or disk having a bore by means of which the plate or disk is slipped over the measuring tube. The plate or disk preferably consists of a semicircular ring portion and a rectangular portion formed thereon, the semicircular ring portion being coaxial with the bore. Advantageously, the plate or disk has a thickness equal to approximately half the diameter of the measuring tube.

According to a development of the first variant of the invention and its embodiments, the measuring tube is provided with an annular rib on the inlet side and an annular rib on the outlet side which are disposed at the locations of the respective sensors.

In a fourth preferred embodiment of the first variant of the invention, the excitation arrangement consists of a first portion which acts on the measuring tube in the direction of the intersection of a longitudinal axis of symmetry of the cantilever and the longitudinal axis of the measuring tube with a first excitation force, and a second portion, which acts on an end of the cantilever remote from the measuring tube with a second excitation force directed opposite to the first excitation force.

A second variant of the invention provides a Coriolis mass flow/density sensor which can be installed in a pipe and through which a fluid to be measured flows during operation, comprising:

a single straight measuring tube having an inlet end and an outlet end;

an inlet plate fixed at the inlet end and surrounding the measuring tube;

and outlet plate fixed at the outlet end and surrounding the measuring tube;

a first support plate fixed to the inlet plate and the outlet plate and extending parallel to a first generating line of the measuring tube;

a second support plate fixed to the inlet plate and the outlet plate and extending parallel to a second generating line of the measuring tube diametrically opposite the first generating line;

a cantilever which is fixed to the measuring tube midway between the inlet end and the outlet end, and which during operation causes the measuring tube to vibrate either in a first fundamental flexural mode or in a second fundamental flexural mode having a higher frequency than the first fundamental flexural mode;

a longitudinal bar located opposite the cantilever and fixed to the first and second support plates, said longitudinal bar acting as a counterbalance;

an excitation arrangement which constantly excites the measuring tube in the second fundamental flexural mode, and which is disposed approximately midway between the inlet end and the outlet end; and a sensor for the motions of the measuring tube on an inlet side and a sensor for the motions of the measuring tube on an outlet side which are located between the middle of the measuring tube and the inlet end and outlet end, respectively, at the same distance therefrom.

In a first preferred embodiment of the second variant of the invention, the cantilever is a plate having a front surface, a back surface, an axis of torsional vibration parallel to the axis of the measuring tube, and a bore by means of which the plate is slipped over the measuring tube, said plate consisting of a circular-segment portion, which is coaxial with the bore, and a rectangular portion formed thereon, an end surface of which, which is cut centrally by a diameter of the measuring tube, is fixed to a fastening area of a beam which is longer than the end surface and has a first end and a second end which project beyond the end surface and comprise respective continuations of the fastening area.

According to a development of this first embodiment of the second variant of the invention, the excitation arrangement consists of a first excitation system, fixed to the continuation of the fastening area of the first beam end, and a second excitation system, fixed to the continuation of the fastening area of the second beam end, with the first and second excitation systems comprising a first coil and a second coil, respectively, which in operation are traversed by an exciting current in opposite directions.

According to a second development of the second variant of the invention, which can also be used in the first preferred embodiment of the second variant, in order to suppress modes of vibration other than the second fundamental flexural mode, a first part of a first brake assembly based on the eddy-current principle is fixed to the front surface of the plate in an area in which the axis point through said plate;

a first part of a second brake assembly based on the eddy-current principle is fixed to the back surface of the plate in an area in which the axis of torsional vibration has a possible piercing point through said plate;

the first brake assembly comprises a second part which is attached to a first holder fixed at least to the first support plate; and the second brake assembly comprises a second portion which is attached to a second holder fixed at least to the first support plate.

In a preferred embodiment of the first development of the second variant of the invention, the first parts of the brake assemblies are circular cylindrical permanent magnets, and the second parts of the brake assemblies are copper disks.

The two variants of the invention and their embodiments and developments may be further improved by extending the measuring tube beyond the inlet and outlet ends using respective tube sections of equal length whose respective free ends are fixed in a housing.

According to a further development of the invention, in addition to the second fundamental flexural mode, the first fundamental flexural mode is excited.

One advantage of the invention is that the accuracy of the mass flow measurement is excellent over a wide density range (0 kg/m$^3$ to 3000 kg/m$^3$; 0 kg/m$^3$ corresponds to a null measurement with a vacuum in the measuring tube). Mass flow/density sensors of a preproduction series, for example, showed accuracies within 0.1% of the measured value.

Another important advantage of the invention is that it is also well suited for measuring the viscosity of the fluid, which is based on the following facts, which are familiar to those skilled in the art:

The viscosity of a fluid can be measured with a Coriolis mass flow/density sensor only if the measuring tube or tubes of the sensor (also) perform a torsional vibration, so that shear forces are exerted on the fluid. In the case of straight measuring tubes excited in flexural modes of vibration, no torsional vibrations, and thus no shear forces, occur at all.

In the case of bent, particularly U-shaped, measuring tubes, torsional vibrations do occur, but their amplitude is so small that a viscosity measurement is virtually impossible. Patent documents in which viscosity is mentioned in connection with Coriolis mass flow/density sensors are not very numerous.

U.S. Pat. No. 4,938,075, for example, only mentions the Navier-Stokes equation, which includes the shear viscosity, which is not measured, however. Other patent specifications deal only with the viscosity compensation of the measured mass-flow values; see, for example, U.S. Pat. Nos. 5,027, 662, 4,876,879, and 4,872,351.

Single-tube Coriolis mass flow/density sensors according to the invention perform not only the flexural vibration required and desired for mass-flow and density measurements but also, because of the cantilever, a torsional vibration in the second fundamental flexural mode around an axis whose position is explained below.

In the invention, the amplitude of this torsional vibration is sufficient to permit the viscosity of the fluid to be measured in addition to mass flow and density with only little additional electronic circuitry.

For this viscosity measurement, recourse can be had to methods described in the literature which discuss this measurement in connection with the measurement of fluid density using vibrating mechanical arrangements, particularly tubes.

According to the journal "IEEE Transactions on Industrial Electronics and Control Instrumentation", August 1980, pages 247 to 253, for example, viscosity can be determined if the resonance quality factor of the vibrating mechanical arrangement, including the fluid, is measured. This can be done, for example, by measuring the electric current with which the arrangement is excited.

BRIEF DESCRIPTION OF THE DRAWINGS

The invention will become more apparent from the following description of embodiments when taken in conjunction with the accompanying drawings, in which like parts are designated by like reference characters. In the drawings.

DETAILED DESCRIPTION OF THE DRAWINGS

Figure 1:
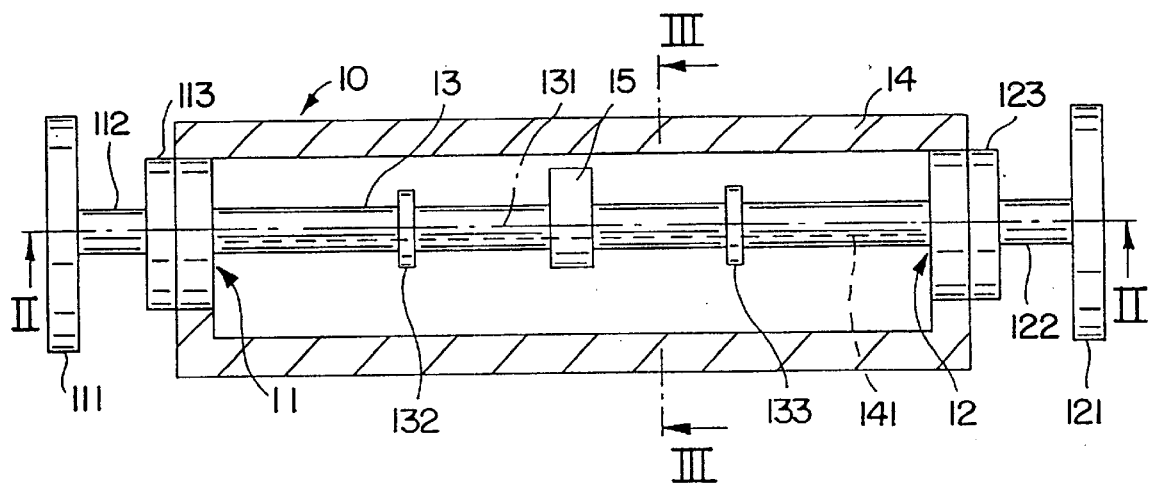
FIG. 1 is a longitudinal view, partially in section, of a first embodiment of a Coriolis mass flow/density sensor according to the first variant of the invention.
Figure 2:
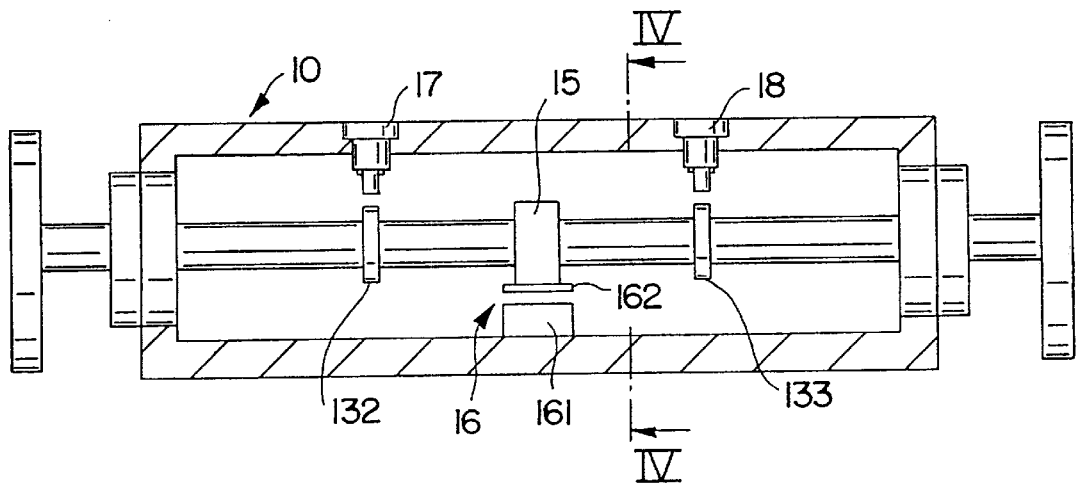
FIG. 2 is a section taken along line A—A of FIG. 1.

The partially sectioned longitudinal view of FIG. 1 shows a Coriolis mass flow/density sensor 10 according to the first variant of the invention, and FIG. 2 shows a section taken along line A—A of FIG. 1. When in use, the mass flow/density sensor 10 is installed in a pipe of a given diameter through which flows a fluid to be measured, the pipe being not shown for the sake of clearness. The sensor is connected to the pipe fluid-tight.

FIGS. 1 and 2 show flanges 111 and 121 for this purpose, which are connected via short tube sections 112 and 122 to end pieces 113 and 123, respectively, in which terminate and are fixed an inlet-end portion 11 and an outlet-end portion 12, respectively, of a single measuring tube 13; the measuring tube is straight and has a longitudinal axis 131. Mass flow/density sensor 10 may also be installed in the pipe via conventional fixing means other than flanges 111, 121.

Inlet end 11 and outlet end 12 of measuring tube 13 are fixed to a support in the form of, e.g., an open or closed frame or a cylindrical tube 14. The closed frame or the cylindrical tube enclose the measuring tube 13 in the manner of an encasement. Measuring tube 13 and end pieces 113, 123 as well as the latter and the support are preferably welded together.

The support has a longitudinal centroidal axis 141 which is parallel to, but does not coincide with, the longitudinal axis 131 of measuring tube 13. This noncongruence is apparent from FIGS. 3 and 4, which show sections taken along line B—B of FIG. 1 and line C—C of FIG. 2, respectively.

Each of FIGS. 1 to 4 shows a circular cylindrical tube 14 of uniform wall thickness. The longitudinal centroidal line of tube 14 is therefore identical with the longitudinal axis of the tube, and measuring tube 13 and tube 14, because of the above-mentioned parallelism of their axes, are not concentric, i.e., not coaxial.

Figure 3:
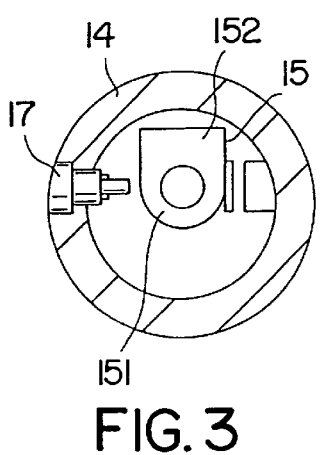
FIG. 3 is a section taken along line B—B of FIG. 1.
Figure 4:
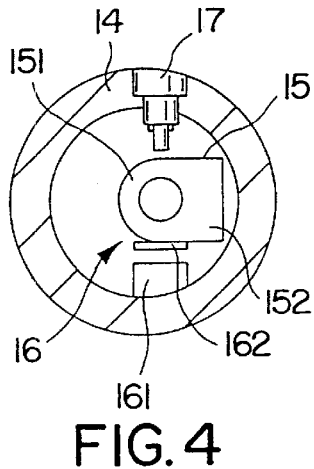
FIG. 4 is a section taken along line C—C of FIG. 2.

Fixed to measuring tube 13 midway between end pieces 113, 123 is a cantilever 15, which may be a plate or disk with a bore by means of which the plate or disk is slipped over measuring tube 13. In FIGS. 3 and 4 it can be seen that in the embodiments shown therein, the plate consists of a semicircular ring portion 151, which is coaxial with the bore, and a rectangular portion 152 integrally formed thereon.

Figure 5:
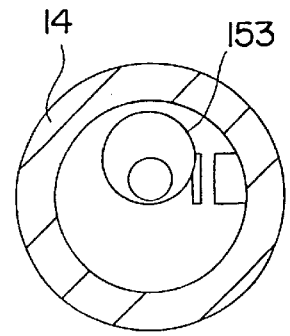
FIG. 5 is a sectional view, similar to FIG. 3, of a modification of the Coriolis mass flow/density sensor of FIGS. 1 to 4.

FIG. 5, a sectional view similar to FIGS. 3 and 4, shows that the cantilever 15 may also be a circular disk 153 which is slipped over measuring tube 13 by means of an eccentric bore and is fixed on this tube. Circular disk 153 and measuring tube 13 are thus not concentric.

The plate or disk serving as cantilever 15 in FIGS. 2 to 5 preferably has a thickness equal to approximately half the diameter of measuring tube 13.

In FIGS. 2 to 4, an excitation arrangement 16 can be seen which is disposed approximately midway between end pieces 113, 123. It is, for example, an electromagnetic shaker comprising, for example, a coil assembly 161, mounted on the support or tube 14, and a permanent magnet 162, attached to cantilever 15.

The excitation arrangement may be any of the various types of excitation arrangements described for this purpose in the prior art relating to Coriolis mass flow/density sensors and Coriolis mass flow meters.

The excitation arrangement may also consist of a first portion, which acts on the measuring tube in the direction of the intersection of a longitudinal axis of symmetry of the cantilever and the longitudinal axis of the measuring tube with a first excitation force, and a second portion, which acts on an end of the cantilever remote from the measuring tube with a second excitation force directed opposite to the first excitation force (not shown for the sake of simplicity).

In operation, excitation arrangement 16 excites measuring tube 13 in flexural modes of vibration whose frequency is equal to the mechanical resonance frequency of the measuring tube. This resonance frequency, as has been known for decades also in connection with Coriolis mass flow sensors, is a measure of the density of the fluid to be measured, cf., for example, U.S. Pat. No. 4,187,721. Further details of the excitation of vibrations are given below in connection with the explanation of FIGS. 12 and 13.

FIG. 2 also shows schematically a sensor 17 for the motions of measuring tube 13 on the inlet side, which can also be seen in FIGS. 3 and 4, and a sensor 18 for the motions of measuring tube 13 on the outlet side. The sensors 17 and 18 are located between the middle of the measuring tube and inlet-end piece 113 and outlet-end piece 123, respectively, at the same distance therefrom. Preferably, annular ribs 132, 133 are provided on measuring tube 13 at the locations of the respective sensors.

For the sensors 17, 18, the various types of sensors described for this purpose in the prior art relating to Coriolis mass flow/density sensors and Coriolis mass flow meters can be used, such as displacement, velocity, or acceleration sensors which operate electrodynamically or optically, for example.

FIGS. 6 to 11, in sectional views corresponding to FIG. 1, show different implementations of a second embodiment of the first variant of the invention using a tube 14' which is again circular cylindrical in terms of its inside diameter, but which, unlike the first embodiment, shown in FIGS. 1 to 5, has only a partially uniform wall thickness, so that its longitudinal centroidal line does not coincide with the longitudinal axis of tube 14'.

On the other hand, this longitudinal axis of tube 14' coincides with the longitudinal axis of measuring tube 13. The two tubes in FIGS. 6 to 11 are thus coaxial although tube 14' does not have a uniform wall thickness. This coincidence, however, is not mandatory: The two longitudinal axes may also be parallel to each other.

In the implementations of FIGS. 6 to 11, the mandatory parallelism of the longitudinal axis of measuring tube 13 and the longitudinal centroidal line of the support, particularly of tube 14', follows from the nonuniform wall thickness of tube 14'. As a result of this nonuniform wall thickness, the wall of tube 14' acts as a counterbalance to cantilever 14, i.e., the unbalance caused by the cantilever is offset.

Figure 6:
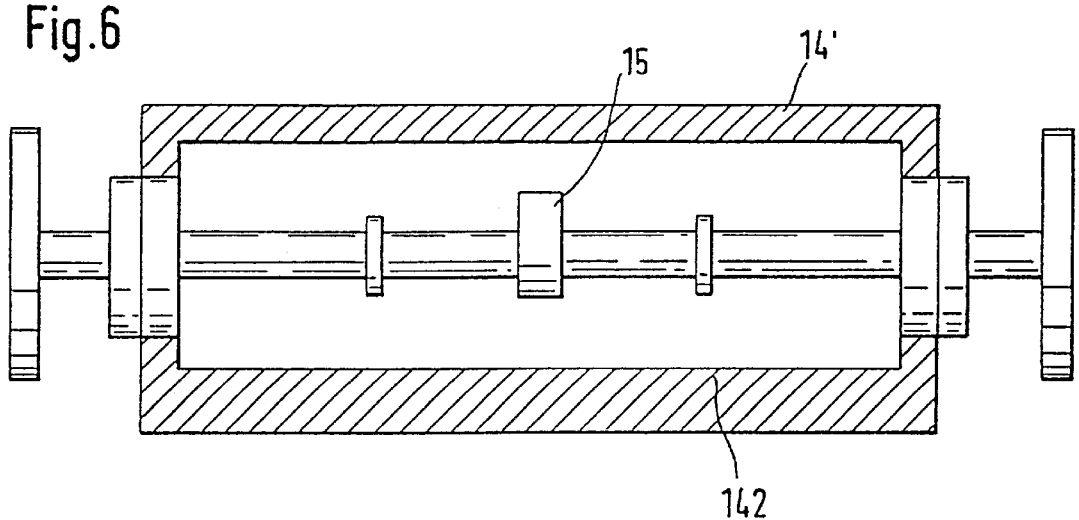
FIG. 6 is a sectional view, corresponding to FIG. 1, of a first implementation of a second embodiment of the first variant.

In the first implementation of the counterbalance, shown in FIG. 6, the wall of tube 14' along a first generating line diametrically opposite cantilever 15 is thicker than the uniform wall thickness of the remainder of this tube over the entire length. This can be achieved, for example, by providing a longitudinal rib 142 along the first generating line, particularly by welding or soldering it on. The width and height of the longitudinal rib and its material must be selected taking into account the mass of cantilever 15 and the uniform wall thickness of tube 14'.

Figure 7:
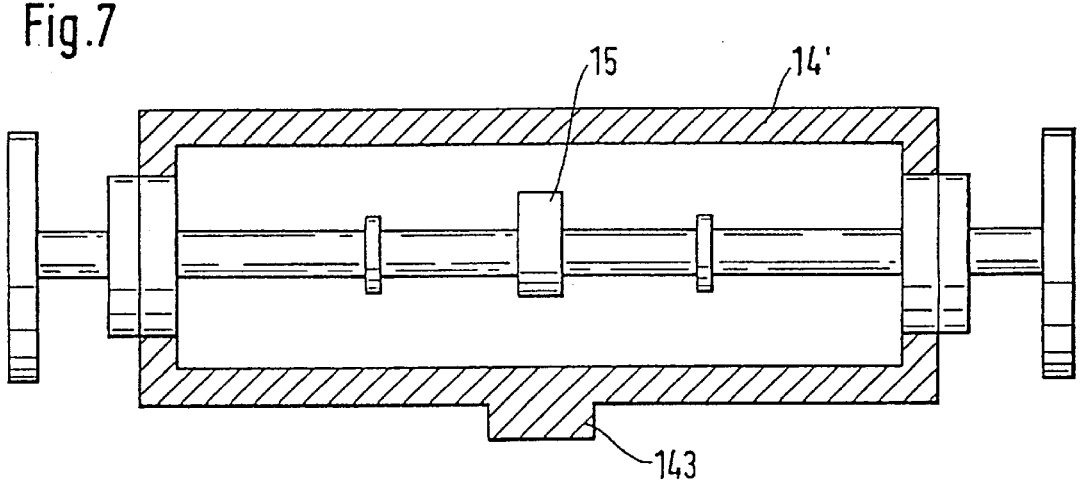
FIG. 7 is a sectional view, corresponding to FIG. 1, of a second implementation of the second embodiment of the first variant.

In the second implementation of the counterbalance, shown in FIG. 7, the wall of tube 14' along the first generating line diametrically opposite cantilever 15 is thickened only in a region opposite cantilever 15 by a counterweight 143.

Counterweight 143 may again be fixed on tube 14' by being welded or soldered on, for example, or it may be inserted into and fixed in a bore or a blind hole made in the wall of the tube, or it may be formed integrally with the tube as shown. The width, height, and length of counterweight 143 and its material must be selected taking into account the mass of cantilever 15 and the uniform wall thickness of tube 14'.

Figure 8:
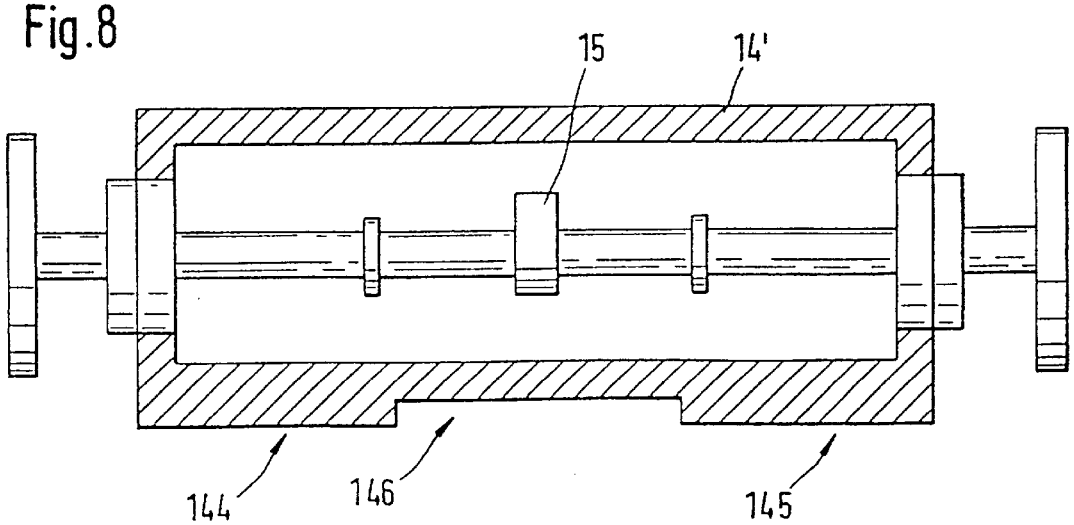
FIG. 8 is a sectional view, corresponding to FIG. 1, of a third implementation of the second embodiment of the first variant.

In the third implementation of the counterbalance, shown in FIG. 8, the wall of tube 14' along the first generating line diametrically opposite cantilever 15 is thicker than the uniform wall thickness of the remainder of tube 14 only over two sections 144, 145 of the entire length. Sections 144, 145 extend from the respective ends of tube 14' toward the middle of the tube, thus forming a central section 146 which has the uniform wall thickness of tube 14'.

The thickening in sections 144, 145 may again be achieved, for example, by welding or soldering respective longitudinal ribs to tube 14' or forming such ribs integrally with the tube. The width, height, length, and material of sections 144, 145 must be selected taking account of the mass of cantilever 15 and the uniform wall thickness of tube 14'.

Figure 9:
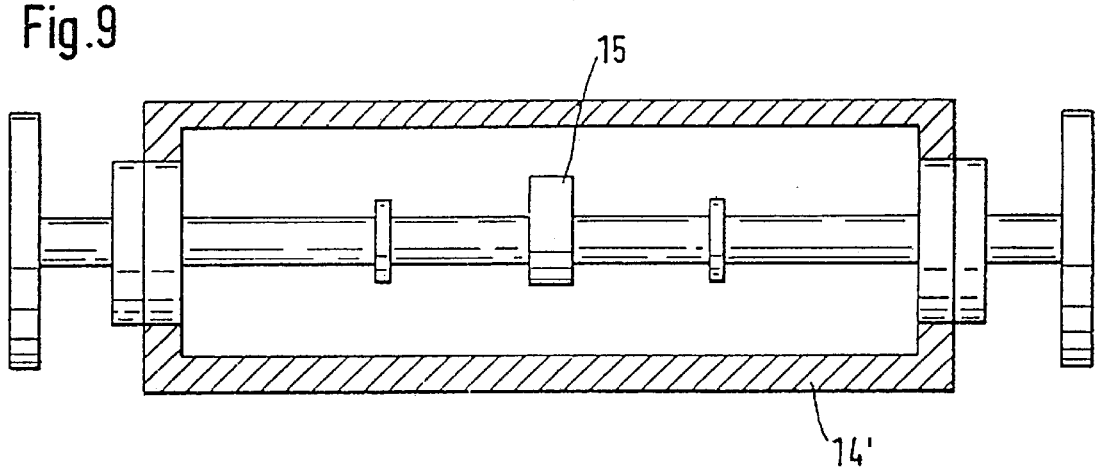
FIG. 9 is a sectional view, corresponding to FIG. 1, of a fourth implementation of the second embodiment of the first variant.

In the fourth implementation of the counterbalance, shown in FIG. 9, the wall of tube 14' along a second generating line adjacent to cantilever 15 was made thinner than the uniform wall thickness of the remainder of the tube over its entire length.

Figure 10:
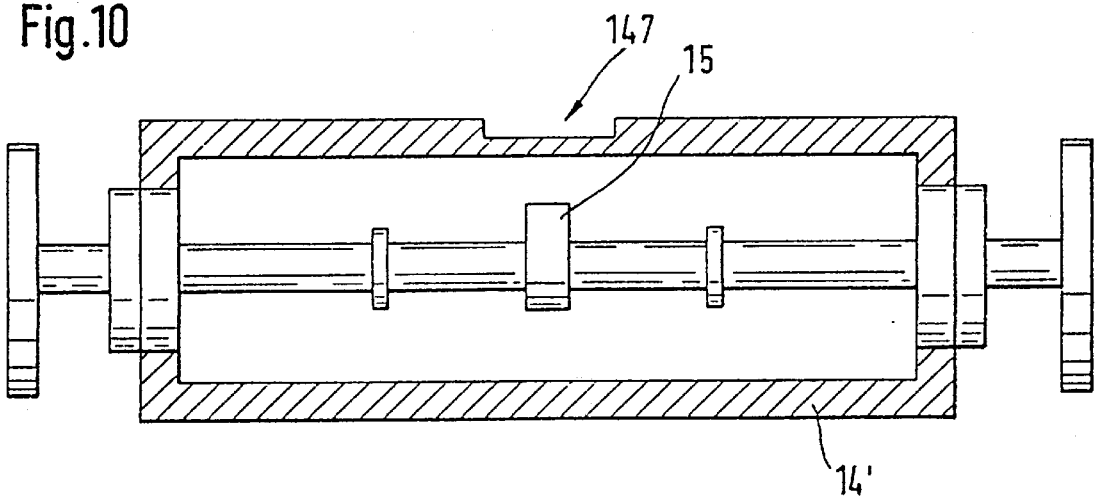
FIG. 10 is a sectional view, corresponding to FIG. 1, of a fifth implementation of the second embodiment of the first variant.

In the fifth implementation of the counterbalance, shown in FIG. 10, the wall of tube 14' along the second generating line adjacent to cantilever 15 was made thinner only in a central section 147 opposite cantilever 15 by removing material from the wall; the remainder of tube 14 has the uniform wall thickness.

Figure 11:
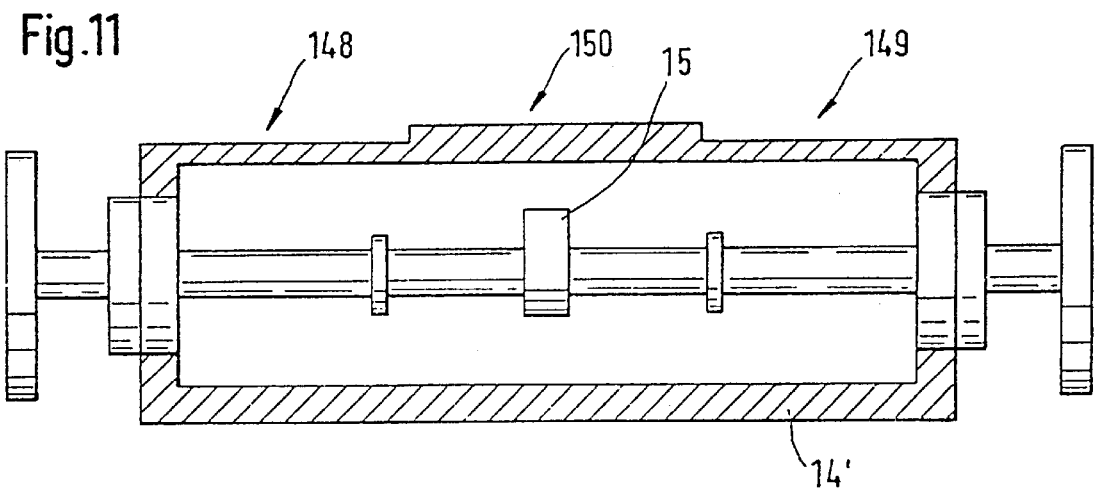
FIG. 11 is a sectional view, corresponding to FIG. 1, of a sixth implementation of the second embodiment of the first variant.

In the sixth implementation of the counterbalance, shown in FIG. 11, the wall of tube 14' along the second generating line adjacent to cantilever 15 was made thinner than the uniform wall thickness of the remainder of the tube over two sections 148, 149 of its entire length. Sections 148, 149 extend from the respective ends of tube 14' toward the middle of the latter, thus forming a central section 150 which has the uniform wall thickness of tube 14'.

In the case of the mass flow/density sensors of FIGS. 9 to 11, the reduction in the wall thickness of tube 14' is achieved by removing, e.g., planing or milling, material from the wall of the tube along the second generating line. The respective mass of the material to be removed must be determined taking into account the mass of cantilever 15 and the uniform wall thickness of tube 14'.

Figure 12:
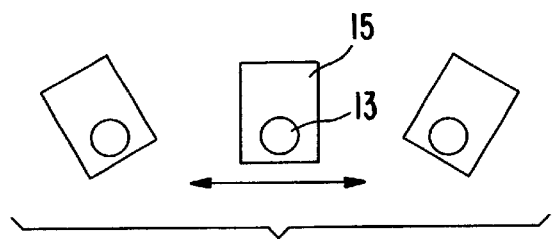
FIG. 12 shows schematically the vibration response of the measuring tube and the cantilever in the first fundamental flexural mode, which can be used in the invention.
Figure 13:
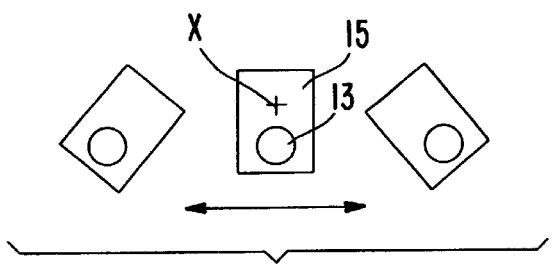
FIG. 13 shows schematically the vibration response of the measuring tube and the cantilever in the second fundamental flexural mode, which is always used in the invention.

As an introduction to the explanation of the FIGS. 12 and 13, it should be recalled that a cantilever-free tube fixed at two points and set into flexural vibration between these points has a single flexural mode of vibration. It vibrates in this mode like a string does at its fundamental resonance frequency, which, in the theory of vibrations, is also referred to as the fundamental tone or first harmonic, and which is numerically the lowest possible resonance frequency. In the steady state, the string, and thus the tube, has a single antinode, and therefore no vibration node, between the two fixing points; vibration nodes are located only at the fixing points.

Unlike such a tube without a cantilever, according to the invention, measuring tube 13, provided with cantilever 15, vibrates in a first and a second flexural mode, as will now be explained with reference to FIGS. 12 and 13. These figures show schematic central cross sections of the vibrator consisting of measuring tube 13 and cantilever 15, with the rest position of the vibrator shown in the middle of each of the figures and the positions of the vibrator at maximum deflection shown at the left and right, cf. the double-headed arrows indicating the direction of vibration.

FIG. 12 shows the conditions for the first fundamental flexural mode of vibration, in which cantilever 15 moves around the axis of measuring tube 13 toward the left when the measuring tube moves to the left, and toward the right when the measuring tube moves to the right. As the cantilever rotates slightly outward, the measuring tube performs a pure flexural vibration.

This first fundamental flexural mode has a—"first"—resonance frequency corresponding to the above-mentioned resonance frequency which is numerically the lowest possible frequency; for a given measuring tube of a predetermined diameter, predetermined length, and predetermined wall thickness and a cantilever with a predetermined mass and predetermined dimensions, this frequency is 400 Hz, for example.

FIG. 13 shows the conditions for the above-mentioned second fundamental flexural mode of vibration, in which cantilever 15 moves about the axis of measuring tube 13 toward the right when the measuring tube moves to the left, and toward the left when the measuring tube moves to the right, i.e., the cantilever rotates inward. Thus, a torsional vibration is superimposed on the flexural vibration which the measuring tube performs like in the first fundamental flexural mode.

The axis of this torsional vibration is obviously not the same as the axis of the measuring tube but is parallel to this axis. The axis of torsional vibration is identical with the centroidal line of all mechanical masses which contribute to the vibration in the second fundamental flexural mode. These are the masses of the measuring tube, including the mass of the fluid, the mass of the cantilever, the mass of the parts of the excitation arrangement fixed to and vibrating with the cantilever, and, if present, the first parts of the brake assembly explained below.

In FIG. 13, a possible piercing point of the axis of torsional vibration through the plane of the paper is denoted by X; it is located, as shown, on the vertical centerline of the cantilever if the mass of the excitation arrangement is symmetrical with respect to this centerline. The piercing point X moves back and forth slightly as a function of the density of fluid.

The second fundamental flexural mode of vibration has a —"second"—resonance frequency which is higher than the above-defined—"first"—resonance frequency of the first fundamental flexural mode; for the above-mentioned given measuring tube, it is 900 Hz.

According to the invention, measuring tube 13 is constantly excited in the second fundamental flexural mode, in which cantilever 15 moves toward the measuring tube when the latter moves outward, as is shown in FIG. 13 and as was explained above.

As the resonance frequency of the second fundamental flexural mode is, or can be made, twice as high as the resonance frequency of the first fundamental flexural mode, an excitation circuit in the form of a phase-locked loop required to energize the excitation arrangement 16, cf., for example, U.S. Pat. No. 4,801,897, can be readily designed to excite only the second fundamental flexural mode.

Figure 14:
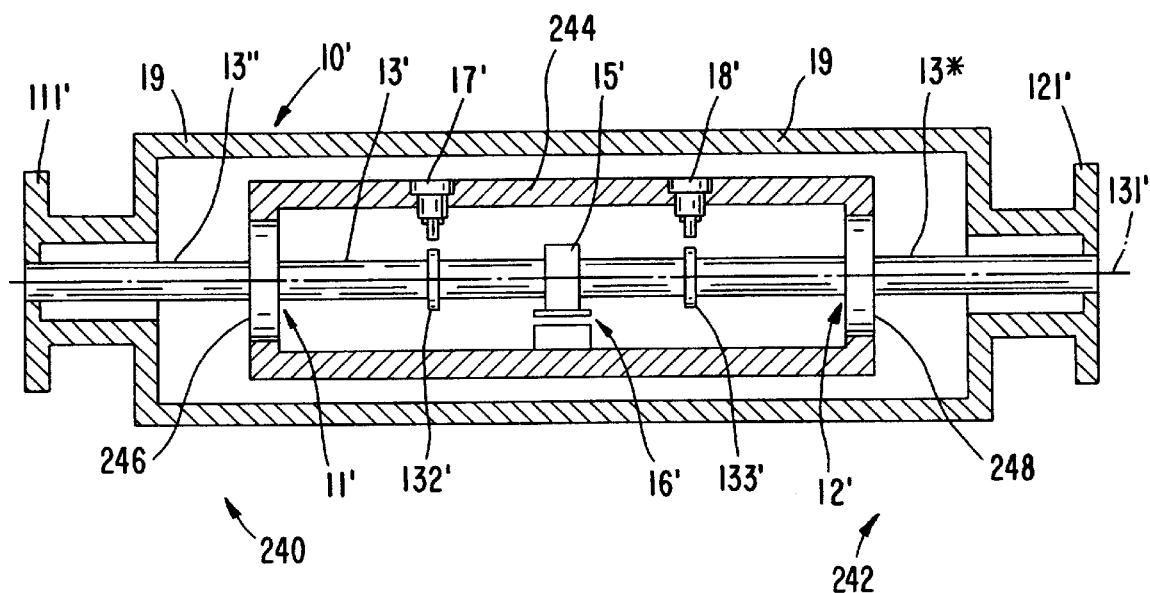
FIG. 14 shows a development of the first variant of the invention in a sectional view similar to FIG. 2.
Figure 15:
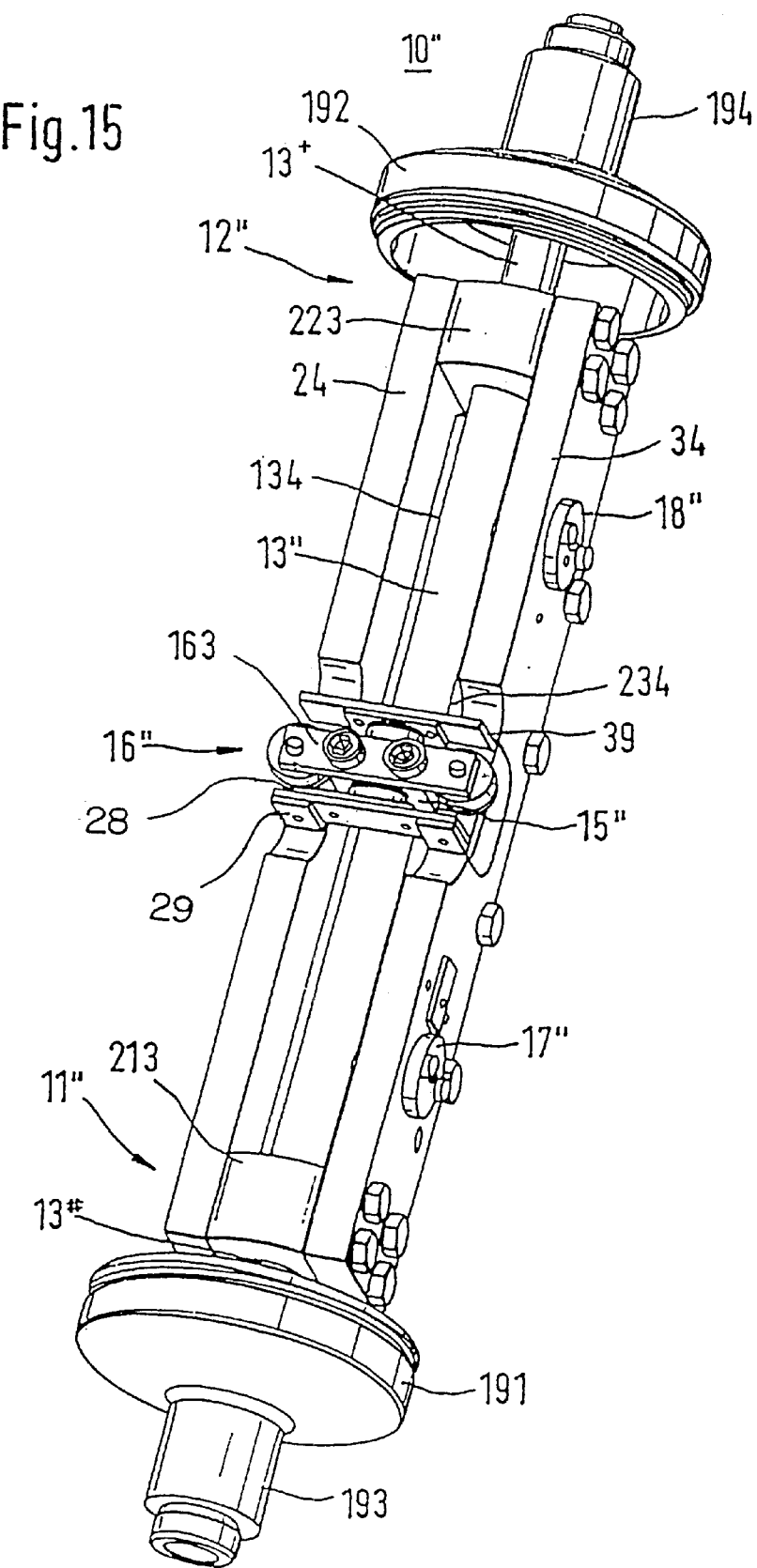
FIG. 15 is a perspective top view of a Coriolis mass flow/density sensor according to the second variant of the invention.
Figure 16:
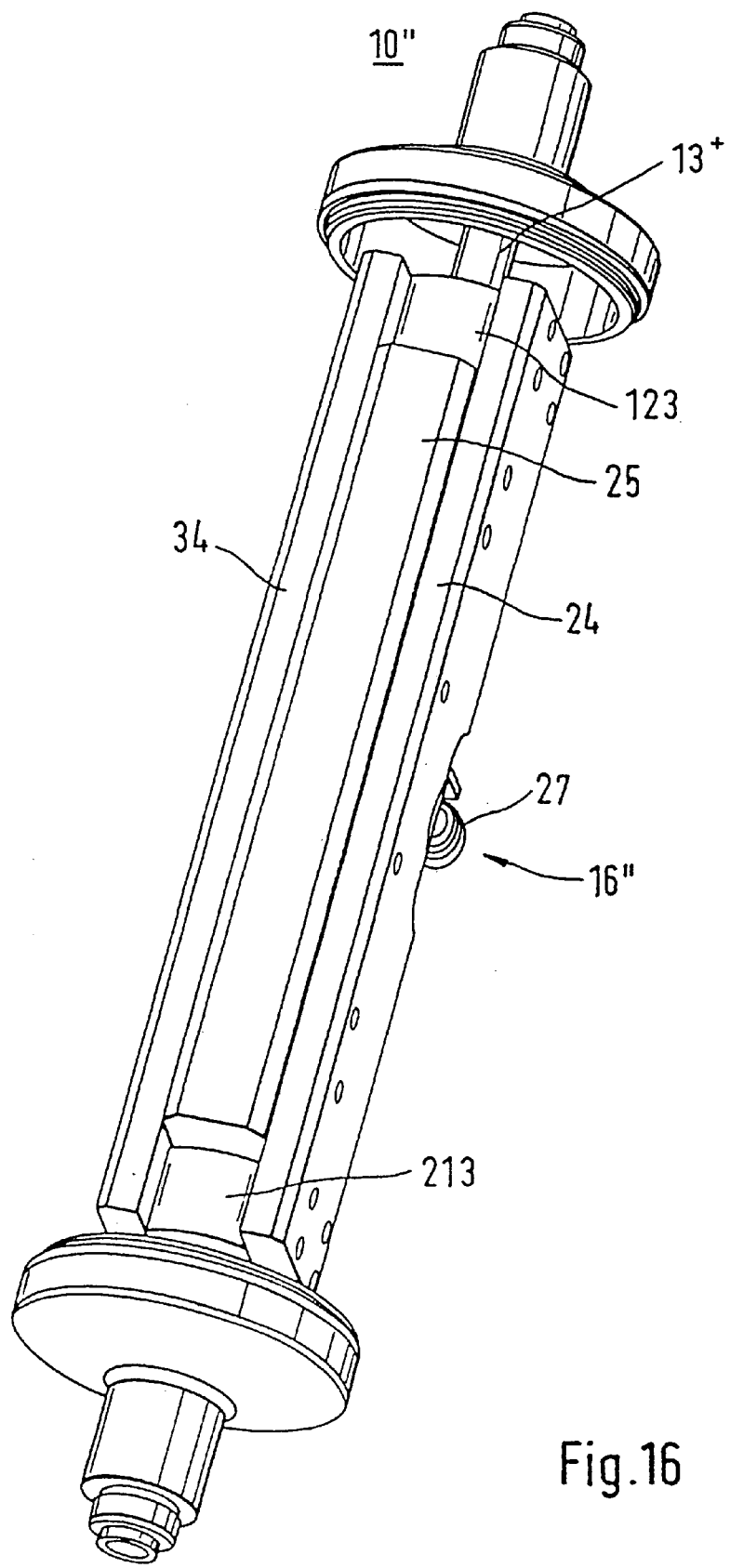
FIG. 16 is a perspective bottom view of the Coriolis mass flow/density sensor of FIG. 15.

FIG. 14, a representation similar to FIG. 2, shows a development of the first variant of the invention which can be used in all the embodiments explained so far and in the embodiments shown in FIGS. 15 and 16. Reference characters of FIG. 14 corresponding to reference characters used so far have the same numeral but are provided with an asterisk.

In the mass flow/density sensor 10' of FIG. 14, the vibrating measuring tube 13' was lengthened beyond the inlet and outlet ends by means of equally long, straight tube sections 13" and 13*, respectively, which are in alignment with measuring tube 13'. The respective free ends of tube sections 13", 13* are fixed in a housing 19. Housing 19 comprises, for example, flanges 111', 121' corresponding to flanges 111, 121 of FIG. 1.

The perspective top view of FIG. 15 and the perspective bottom view of FIG. 16 show a second variant of a Coriolis mass flow/density sensor 10" according to the invention. This sensor has a single straight measuring tube 13" with an inlet end 11' and an outlet end 12". An inlet plate 213 and an outlet plate 223 which completely surround the measuring tube 13" are fixed at the inlet end and the outlet end, respectively.

Fixed to inlet plate 213 and outlet plate 223 is a first support plate 24, which extends parallel to a first generating line 134 of measuring tube 13". Also fixed to the inlet plate and the outlet plate is a second support plate 34, which extends parallel to a second generating line 234 of the measuring tube diametrically opposite to the first generating line 134. Thus, side surfaces of the two support plates 24, 34 facing toward each other are also parallel to each other.

Fixed on measuring tube 13" approximately midway between inlet end 11" and outlet end 1211 is a cantilever 15" which in operation causes measuring tube 13" to vibrate either in a first fundamental flexural mode or in a second fundamental flexural mode having a higher frequency than the first fundamental flexural mode.

The member acting as counterbalance in the second variant is a longitudinal bar 25 which is located opposite to cantilever 15" and is fixed to the first and second support plates 24, 34. In FIGS. 15 and 16, longitudinal bar 25 extends substantially parallel to the entire vibratory length of measuring tube 13"; this is not mandatory, however; it is so in this embodiment only.

The system consisting of the two support plates 24, 34, inlet plate 213, outlet plate 223, and longitudinal bar 25 has a longitudinal centroidal line parallel to the axis of measuring tube 13". With respect to this property, the arrangement of FIGS. 15 and 16 is thus comparable with the arrangement of FIGS. 1 to 5.

Measuring tube 13" is excited in the second fundamental flexural mode of vibration by an excitation arrangement 16" which acts on cantilever 15" and is thus again disposed approximately midway between the inlet end and the outlet end. Special details of the excitation arrangement will be explained below in connection with FIG. 17.

The motions of measuring tube 13" on the inlet and outlet sides are sensed with sensors 17" and 18", respectively, which are located between the middle of the measuring tube and the inlet and outlet ends, respectively, at the same distance therefrom.

In FIGS. 15 and 16, it is indicated by the heads of the screws shown that the above-mentioned fixing of support plates 24, 34 to end plates 213, 223 and to longitudinal bar 25 may be done by screwing. This is not mandatory, however; it is also possible to use other suitable forms of fastening familiar to those skilled in the art.

The second variant, shown in FIGS. 15 and 16, is similar in the design of its mechanical vibrating system to the development of the first variant shown in FIG. 14. In the second variant, too, measuring tube 13" was lengthened beyond the inlet and outlet ends by means of equally long, straight tube sections 13# and 13+, respectively, which are aligned with measuring tube 13".

The respective free ends of tube sections 13#, 13+ are fixed in a housing, of which only housing caps 191, 192 are shown, while a remaining, tube like part which interconnects and hermetically seals the housing caps 191, 192 is not illustrated so as not to cover the internal parts shown.

FIGS. 15 and 16 also show that housing caps 191 and 192 have respective connecting portions 193 and 194 formed thereon via which the Coriolis mass flow/density sensor 10" can be installed in the above-mentioned pipe fluid-tight.

Figure 17:
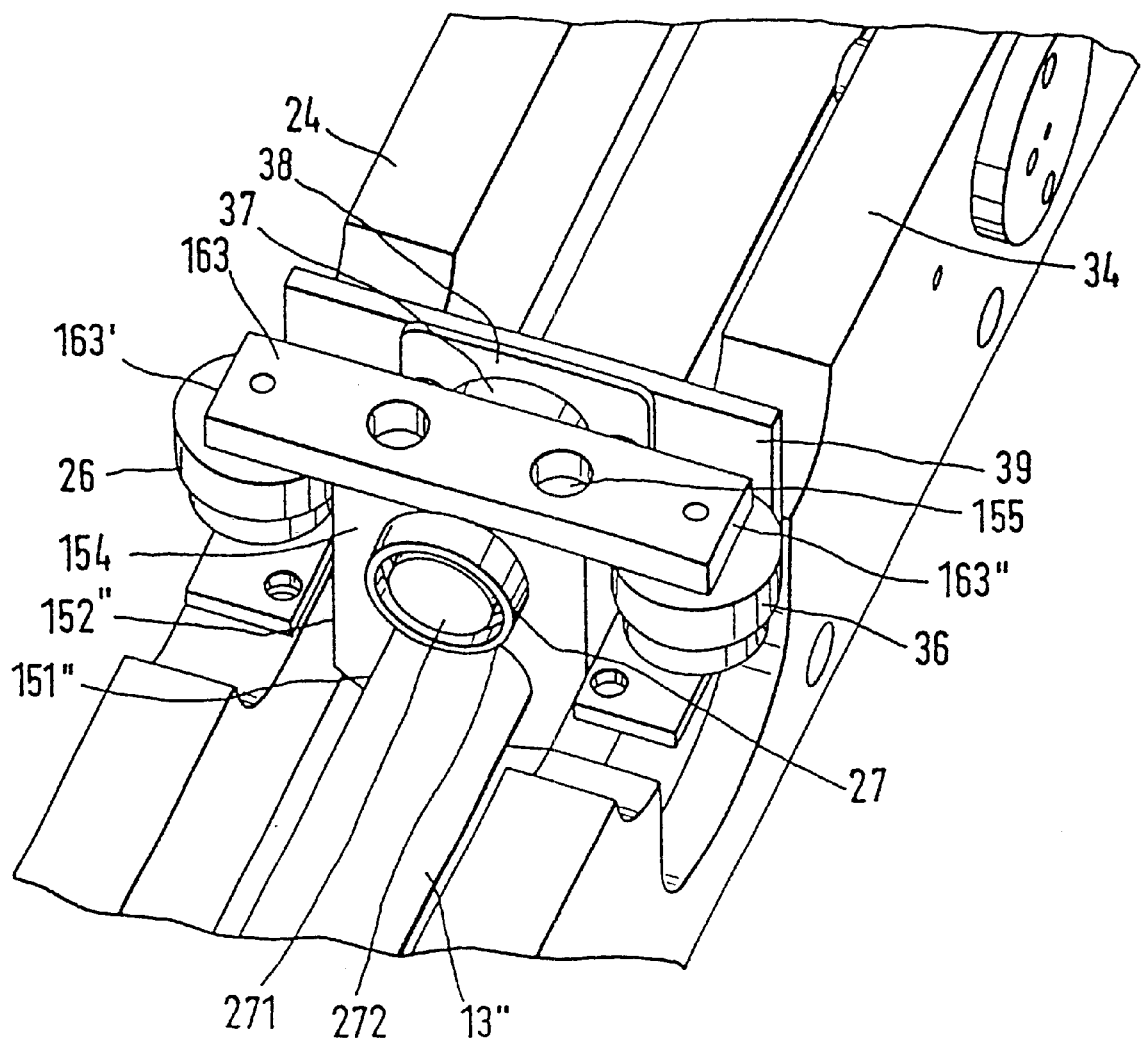
FIG. 17 is a scaled-up perspective top view of an important detail of FIG. 15.

FIG. 17 is a scaled-up perspective top view of the cantilever 15" and the excitation arrangement 16" of FIG. 15 and of further parts preferably associated with the excitation arrangement. In a preferred embodiment of the second variant of the invention, cantilever 15" is implemented as a plate. It has a front surface 154 and a parallel back surface, which is not visible in FIGS. 15 and 17. Cantilever 15" has a bore by means of which the plate is slipped over and fixed on measuring tube 13".

The plate—similarly as in the arrangement of FIGS. 1 to 4—consists of a circular-segment portion 151", which is coaxial with the bore, and a rectangular portion 152" integrally formed thereon. An end surface 155 of rectangular portion 152" is cut centrally by a diameter of measuring tube 13"; only a small portion of this end surface can be seen in FIG. 17, namely in bores of a beam 163.

Beam 163 is fixed in a fastening area (not visible) to end surface 155. Screws used for this purpose can be seen in FIG. 15. Beam 163 is longer than end surface 155 and has a first end 163' and a second end 163" with respective continuations of the fastening area, which ends project beyond side surface 155.

The excitation arrangement 16" consists of a first excitation system 26, fixed to the continuation of the fastening area of the first beam end 163', and a second excitation system 36, fixed to the continuation of the fastening area of the second beam end 163". The first excitation system 26 contains a first coil fixed to support plate 24, and the second excitation system 36 contains a second coil fixed to support plate 34. In operation, the first and second coils are traversed by an exciting current in opposite directions. The coils cooperate with first and second permanent magnets fixed to beam ends 163' and 163", respectively.

According to a further development of the invention, in order to suppress modes of vibration other than the second fundamental flexural mode, particularly in order to suppress the first fundamental flexural mode and its harmonics, a first part 27 and a second part 37 of a brake assembly based on the eddy-current principle are provided.

The first part 27 is fixed to front surface 154 of the plate in an area where the above-explained axis of the mechanical torsional vibration system has a possible piercing point through front surface 154.

In similar fashion, the first part 37 of the second brake assembly is fixed to the back surface of the plate in an area where the above-mentioned axis of torsional vibration has a possible piercing point through the back surface of the plate.

A second part of the first brake assembly, which part is hardly visible in FIG. 15 and, therefore, is not provided with a reference numeral—it should be the reference numeral 28—is secured to a first holder 29 fixed to the first and second support plates 24, 34. This holder is only shown in FIG. 15; in FIG. 17 it has been omitted in order not to obstruct the view of cantilever 15" etc.

A second part 38 of the second brake assembly is secured to a second holder 39 fixed to the first and second support plates 24, 34, namely by means of angled "foots", as shown. The two holders are preferably made of soft magnetic material.

The two first parts 27, 37 of the brake assemblies comprise circular cylindrical permanent magnets, of which only permanent magnet 261 can be seen in FIG. 17 together with an associated holder 272. The two second parts of the brake assemblies are copper disks.

By means of the brake assemblies, the instantaneous position of the above-mentioned axis of torsional vibration is stabilized. This prevents the building up of another vibration mode, particularly the first fundamental flexural mode and its harmonics, and/or of those harmonics of the second fundamental flexural mode which have an axis of torsional vibration other than the latter.

The buildup of such a mode or of such harmonics would be equivalent to a considerable back-and-forth motion of the axis of torsional vibration, cf., for example, FIG. 12. This stabilization takes place as long as the axis of torsional vibration is in the area of the second parts 28, 38 of the brake assemblies.

A further increase in measurement accuracy is possible in both variants of the invention if in addition to the second fundamental flexural mode, the first fundamental flexural mode is excited; then, the brake assemblies of FIGS. 15 and 17 must, of course, be omitted.

The excitation of the first fundamental flexural mode can be achieved by using a further phase-locked loop which operates on the first resonance frequency. In that case, the signals provided by the sensors will contain both a Coriolis-effect-induced phase-shift component of the vibrations of the second resonance frequency and a Coriolis-effect-induced phase-shift component of the vibrations of the first resonance frequency. Since these two resonance frequencies differ by a factor of about 2, the two phase-shift components can be readily separated by electronic means.

What is claimed is:

1. A Coriolis mass flow sensor for measuring a mass flow rate of a fluid flowing through a pipe, said mass flow sensor comprising:

a measuring tube for conducting said fluid, said measuring tube being fixed in a support and coupled to said pipe via an inlet tube and an outlet tube;

an excitation arrangement for vibrating said measuring tube in a predetermined vibration mode;

a sensor arrangement for detecting vibrations of said measuring tube; and a brake assembly coupled to said measuring tube and said support, said brake assembly being operable to suppress at least one mode of vibrations other than said predetermined vibration mode.

2. The Coriolis mass flow sensor of claim 1, wherein said brake assembly is based on an eddy-current principle.

3. The Coriolis mass flow sensor of claim 1, wherein said brake assembly acts on said measuring tube via a cantilever fixed to the measuring tube.

4. The Coriolis mass flow sensor of claim 1, wherein said support is formed as an encasement-part for said measuring tube.

5. A Coriolis mass flow sensor for measuring a mass flow rate of a fluid flowing through a pipe, said mass flow sensor comprising:

a housing having an inlet-end portion and an outlet-end portion axially spaced apart from said inlet-end portion of the housing, a flow tube for conducting said fluid, said flow tube being fixed in the housing and having an inlet-end section, an outlet-end section axially spaced apart from said inlet-end section, and a measuring section between said inlet-end section and said outlet-end section, said inlet-end section of the flow tube extending into said inlet-end portion of the housing and said outlet-end section of the flow tube extending into said outlet-end portion of the housing, said measuring section having an inlet-end portion and an outlet-end portion being located on a longitudinal axis of the flow sensor, said inlet-end portion and said outlet-end portion of said measuring section being spaced apart from said inlet-end portion and said outlet-end portion of said housing, respectively;

an excitation arrangement for vibrating said measuring section;

a sensor arrangement for detecting vibrations of said measuring section; and a counterbalance coupled to said inlet-end portion and said outlet-end portion of the measuring section, said counterbalance having a centroid spaced apart from said longitudinal axis of the flow sensor extending between said inlet-end portion and said outlet-end portion of the measuring section.

6. The Coriolis mass flow sensor of claim 5 wherein the counterbalance is formed by means of a support having an inlet-end portion coupled to the inlet-end portion of said measuring tube and an outlet-end portion coupled to the outlet-end portion of said measuring tube.

7. The Coriolis mass flow sensor as claimed in claim 6 wherein the support is a cylindrical tube having a longitudinal axis which is substantially parallel to said longitudinal axis of the flow sensor.

8. The Coriolis mass flow sensor of claim 5 wherein the flow tube comprises a substantially straight measuring tube section.

9. The Coriolis mass flow sensor of claim 5 wherein the flow tube comprises a substantially straight inlet-end section and a substantially straight outlet-end section.

10. The Coriolis mass flow sensor of claim 5 wherein the flow tube is substantially straight.

11. The Coriolis mass flow sensor of claim 5 wherein the measuring section and said counterbalance are isolated from external vibrations of the housing only by the inlet-end section and the outlet-end section of the flow tube.

12. The Coriolis mass flow sensor of claim 5 wherein during operation the centroid oscillates about said longitudinal axis of the flow sensor at least temporary.

13. The Coriolis mass flow sensor as claimed in claim 5 wherein the sensor arrangement comprises a first sensor for detecting the motions of the measuring section and a second sensor for detecting the motions of the measuring section, the first sensor being located between the middle of the measuring section and said inlet-end section and the second sensor being located between the middle of the measuring section and said outlet-end section.

14. A Coriolis mass flow sensor for measuring a mass flow rate of a fluid flowing through a pipe, said mass flow sensor comprising:

a housing having an inlet-end portion and an outlet-end portion being axially spaced apart from said inlet-end portion of the housing, a measuring tube for conducting said fluid to be measured, said measuring tube being coupled to said inlet-end portion of the housing by means of an inlet-side tube section and to said outlet-end portion of the housing by means of an outlet-side tube section, an excitation arrangement for vibrating said measuring section;

a sensor arrangement for detecting vibrations of said measuring section; and a counterbalance coupled to an inlet-end portion of the measuring tube and to an outlet-end portion of the measuring tube;

said inlet-end portion of the measuring tube and said outlet-end portion of the measuring tube being spaced apart from said inlet-end portion of the housing and said outlet-end portion of the housing, respectively, and said inlet-end portion of the measuring tube and said outlet-end portion of the measuring tube being located on a longitudinal axis of the flow sensor, said counterbalance having a centroid spaced apart from said longitudinal axis extending between said inlet-end portion of the measuring tube and said outlet-end portion of the measuring tube.

15. The Coriolis mass flow sensor of claim 14 wherein the counterbalance is formed by means of a support having an inlet-end portion coupled to the inlet-end portion of said measuring tube and an outlet-end portion coupled to the outlet-end portion of said measuring tube.

16. The Coriolis mass flow sensor as claimed in claim 15 wherein the support is a cylindrical tube having a longitudinal axis which is substantially parallel to said longitudinal axis of the flow sensor.

17. The Coriolis mass flow sensor of claim 14 wherein the flow tube comprises a substantially straight measuring tube section.

18. The Coriolis mass flow sensor of claim 14 wherein the flow tube comprises a substantially straight inlet-end section and a substantially straight outlet-end section.

19. The Coriolis mass flow sensor of claim 14 wherein the flow tube is substantially straight.

20. The Coriolis mass flow sensor of claim 14 wherein the measuring section and said counterbalance are isolated from external vibrations of the housing only by the inlet-end section and the outlet-end section of the flow tube.

21. The Coriolis mass flow sensor of claim 14 wherein the centroid oscillates about said longitudinal axis during operation at least temporary.

22. The Coriolis mass flow sensor as claimed in claim 14 wherein the sensor arrangement comprises a first sensor for detecting the motions of the measuring tube and a second sensor for detecting the motions of the measuring tube, the first sensor being located between the middle of the measuring tube and said inlet-end portion and the second sensor being located between the middle of the measuring tube and said outlet-end portion.

23. A Coriolis mass flow/density sensor which can be installed in a pipe and through which a fluid to be measured flows during operation, comprising;

a measuring tube having an inlet end and an outlet end;

a cantilever being fixed to the measuring tube between the inlet end and the outlet end, and said measuring tube and said cantilever forming a vibrator having a flexural mode of vibration in which the measuring tube performs flexural vibration and torsional vibration, said torsional vibration being superimposed on said flexural vibration, an excitation arrangement for exciting said measuring tube to vibrate in said flexural mode and a sensor arrangement for detecting vibrations of said measuring tube.

24. Coriolis mass flow/density sensor as claimed in claim 23 further comprising a support fixed to the inlet end and the outlet end, said support being coupled to said inlet-end portion of the housing by means of an inlet-side tube section and to said outlet-end portion of the housing by means of an outlet-side tube section, said inlet-side tube section and said outlet-side tube section being connected with the measuring tube.

25. The Coriolis mass flow/density sensor as claimed in claim 24 wherein the support forms a counterbalance for said vibrator.

26. The Coriolis mass flow/density sensor as claimed in claim 24 wherein a counterweight is fixed to, partially inserted in, or integrally formed on a wall of said support, said wall being disposed substantially opposite the cantilever.

27. The Coriolis mass flow/density sensor as claimed in claim 24 wherein the support is a cylindrical tube having a longitudinal axis which is substantially parallel to a longitudinal axis of the flow sensor.

28. The Coriolis mass flow/density sensor as claimed in claim 23 wherein the flexural mode of vibration has one resonance frequency.

29. The Coriolis mass flow/density sensor as claimed in claim 28 wherein the excitation arrangement excites said measuring tube to vibrate at said resonance frequency of said flexural mode of the vibrator.

30. The Coriolis mass flow/density sensor as claimed in claim 23 wherein the measuring tube is substantially straight.

31. A Coriolis mass flow/density sensor as claimed in claim 23 further comprising a housing having an inlet-end portion and an outlet-end portion axially spaced apart from said inlet-end portion of the housing.

32. The Coriolis mass flow/density sensor as claimed in claim 23, wherein the sensor arrangement comprises a first sensor for detecting the motions of the measuring tube and a second sensor for detecting the motions of the measuring tube, the first sensor being located between the middle of the measuring tube and said inlet end of the measuring tube and the second sensor being located between the middle of the measuring tube and said outlet end of the measuring tube.

33. A Coriolis mass flow/density sensor which can be installed in a pipe and through which a fluid to be measured flows during operation, comprising:

a housing having an inlet-end portion and an outlet-end portion axially spaced apart from said inlet-end portion of the housing, a measuring tube having an inlet end and an outlet end;

a cantilever being fixed to the measuring tube between the inlet end and the outlet end; and said measuring tube and said cantilever forming a vibrator having a flexural mode of vibration in which the measuring tube performs flexural vibration and torsional vibration, said torsional vibration being superimposed on said flexural vibration;

an excitation arrangement for exciting said measuring tube to vibrate in said flexural mode;

a sensor arrangement for detecting vibrations of said measuring tube; and a support fixed to the inlet end and the outlet end, said support being coupled to said inlet-end portion of the housing by means of an inlet-side tube section and to said outlet-end portion of the housing by means of an outlet-side tube section, said inlet-side tube section and said outlet-side tube section being connected with the measuring tube.

34. The Coriolis mass flow/density sensor as claimed in claim 33 wherein the excitation arrangement excites said measuring tube to vibrate at a resonance frequency of said flexural mode of the vibrator.

35. The Coriolis mass flow/density sensor as claimed in claim 33 wherein the flexural mode of vibration has one resonance frequency.

36. The Coriolis mass flow/density sensor as claimed in claim 33 wherein the support forms a counterbalance for said vibrator.

37. The Coriolis mass flow/density sensor as claimed in claim 33 wherein a counterweight is fixed to, partially inserted in, or integrally formed on a wall of said support, said wall being disposed substantially opposite the cantilever.

38. The Coriolis mass flow/density sensor as claimed in claim 33 wherein the measuring tube is substantially straight.

39. The Coriolis mass flow/density sensor as claimed in claim 33 wherein the support is a cylindrical tube having a longitudinal axis which is substantially parallel to a longitudinal axis of the flow sensor.

40. The Coriolis mass flow/density sensor as claimed in claim 22 wherein the sensor arrangement comprises a first sensor for detecting the motions of the measuring tube and a second sensor for detecting the motions of the measuring tube, the first sensor being located between the middle of the measuring tube and said inlet end of the measuring tube and the second sensor being located between the middle of the measuring tube and said outlet end of the measuring tube.

* * * * *